United States Patent [19]
Fisher et al.

[11] 4,067,987
[45] Jan. 10, 1978

[54] STABILIZED OXADIAZOLE ANTHELMINTIC COMPOSITIONS

[75] Inventors: Michael H. Fisher, Somerville; George B. Smith, Edison; Dale R. Hoff, Basking Ridge, all of N.J.

[73] Assignee: Merck & Co., Inc., Rahway, N.J.

[21] Appl. No.: 647,848

[22] Filed: Jan. 9, 1976

Related U.S. Application Data

[63] Continuation of Ser. No. 524,010, Nov. 14, 1974, abandoned, which is a continuation-in-part of Ser. No. 234,655, March 14, 1972, Pat. No. 3,863,012.

[51] Int. Cl.² .............................................. A61K 31/42
[52] U.S. Cl. ................................ 424/272; 260/307 G
[58] Field of Search ........................................ 424/272

[56] References Cited

U.S. PATENT DOCUMENTS 3,279,988  10/1966  Buting et al. ........................ 424/272

OTHER PUBLICATIONS

Spiegel et al., "J. Pharm. Sciences", vol. 52, No. 10, (1963), pp. 917, 921–925.
Chemical Abstracts, vol. 68, (1968), p. 96545j.

*Primary Examiner*—V. D. Turner
*Attorney, Agent, or Firm*—David L. Rose; J. Jerome Behan

[57] ABSTRACT

Anthelmintically active 3-loweralkyl-1,2,4-oxadiazoles are stabilized by the formation of homogeneous mixtures thereof with water and with certain alcohols, the molar ratio of stabilizer to oxadiazole being adjusted to within 0.1:1 to 2:1 to achieve required stability.

16 Claims, No Drawings

STABILIZED OXADIAZOLE ANTHELMINTIC COMPOSITIONS

This application is a continuation of application Ser. No. 524,010 filed Nov. 14, 1974, now abandoned, which is a continuation-in-part of Ser. No. 234,655 filed Mar. 14, 1972, which issued to U.S. Pat. No. 3,863,012 on Jan. 28, 1975.

The instant invention relates to methods for stabilizing alkyl substituted oxadiazoles and processes for employing such stabilized oxadiazoles in the treatment and control of helminthiasis. More particularly, the instant invention relates to methods for stabilizing 1,2,4-oxadiazoles characterized by having a loweralkyl group in the three position; to stabilized oxadiazole formulations so formed; and to processes for employing such stabilized formulations as anthelmintic agents.

The disease or group of diseases described generally as helminthiasis is due to infestation of the animal body with parasitic worms known as helminths. Helminthiasis is a prevalent and serious economic problem throughout the world in domesticated animals such as swine, sheep, cattle, goats, horses, dogs and poultry. Among the helminths, the groups of worms described as nematodes and trematodes cause widespread and often serious infections in various animal species. Certain nematodes and trematodes lead also to troublesome infections in humans, particularly in tropical climates. Such parasitic infections can lead to various debilitating effects such as anemia, malnutrition, weakness, weight loss, severe damage to the liver and walls of the intestine and, if uncontrolled, often results in death. Helminthiasis, therefore, is a major medical and veterinary problem and new and useful compositions for the treatment and control of helminthiasis constitute significant advances in the therapeutic arts.

Over the years, a considerable effort has been expended in the search for, and development of, new chemotherapeutic agents which would prove useful in the application of anthelmintic therapy. Numerous compounds have been proposed and many of these have found varying degrees of acceptance as commercial anthelmintic agents. Many compounds, however, of demonstrated anthelmintic activity have never been employed commercially due to a variety of factors including difficulty of manufacture, toxicity to the host or other objectionable side reaction to the host, formulation difficulties or basic instability of the active compound.

Among this group of compounds are the 3-loweralkyl-1,2,4-oxadiazoles. Such oxadiazoles, wherein the alkyl moiety may be either straight or branched chain and may contain from 1 to 4 carbon atoms, such as 3-methyl-1,2,4-oxadiazole, 3-ethyl-1,2,4-oxadiazole, 3-propyl-1,2,4-oxadiazole, 3-isopropyl-1,2,4-oxadiazole, 3-butyl-1,2,4-oxadiazole and 3-isobutyl-1,2,4-oxadiazole have been known to be effective anthelmintic agents (see for example, U.S. Pat. No. 3,279,988). Indeed, these compounds have been recognized as being at least as effective, and possibly as being more effective, as anthelmintic agents than the anthelmintic 1,2,4-oxadiazoles having aryl, aralkyl or heterocyclic substituents in the 3-position. Unfortunately, it has not been possible heretofore to employ these anthelmintically effective 3-alkyl-1,2,4-oxadiazoles as commercial anthelmintic agents due to the inherent instability of the molecule. For example, the compound, 3-methyl-1,2,4-oxadiazole, which displays especially attractive anthelmintic properties, is known to decompose to acetonitrile and cyanuric acid at a rate of about 10% per month in shelf storage at room temperature, i.e. 25° C. (see Moussebois et al., Helv. Chim. Acta, 47838, 1964). Much more rapid decomposition occurs at elevated temperatures as often are encountered during transportation and in shelf storage prior to use in anthelmintic therapy. In laboratory experiments, 3-methyl-1,2,4-oxadiazole is substantially completely decomposed in 4 hours at 100° C. or in 37 hours at 80° C. Similar instability, varying only in degree, is observed in the higher homologs of this series. Quite clearly, compounds displaying so high a degree of instability, despite their recognized anthelmintic activity, could not heretofore be employed commercially as anthelmintic agents. The instant invention is based upon applicants' discovery of a means whereby markedly enhanced stability may be imparted readily to 3-loweralkyl-1,2,4-oxadiazoles thus making available for the first time commercially feasible therapeutic formulations containing these highly effective anthelmintic agents.

Surprisingly, applicants have discovered that 3-loweralkyl-1,2,4-oxadiazoles are rendered sufficiently stable to make feasible their commercial utilization as anthelmintic agents by the addition thereto of water to form homogeneous mixtures. 3-Loweralkyl-1,2,4-oxadiazoles as defined above are miscible with water at room temperature and, indeed, applicants have found that a measurable degree of stability is imparted to such oxadiazoles by the addition thereto of water over a wide range of concentration (e.g. from 0.1 to 10 moles of water per mole of oxadiazole). The degree of stabilization achieved, however, is directly dependent upon the molar ratio of water to oxadiazole in the mixture. Applicants have found that in order to obtain aqueous solutions of 3-loweralkyl-1,2,4-oxadiazoles wherein the oxadiazole is sufficiently stable to make feasible its commercial utilization in anthelmintic therapy, it is necessary that the molar ratio of water to oxadiazole be adjusted within a critical range. Thus, it has been found that the requisite degree of stability is achieved when the molar ratio of water to oxadiazole falls within the range of about 0.5:1 to about 2:1. Preferably, the molar ratio of water to oxadiazole is adjusted to fall within the range of about 0.75:1 to about 1.25:1 and maximum stability is achieved when the molar ratio of water to oxadiazole is 1:1. Accordingly, it is contemplated that aqueous 3-loweralkyl-1,2,4-oxadiazole formulations having a molar ratio of water to oxadiazole as defined above will be employed in the treatment and control of helminthiasis.

The stabilizing effect of water on 3-loweralkyl-1,2,4-oxadiazoles as observed by applicants, has been studied and confirmed by standard laboratory procedures. Thus, for example, kinetic data of the decomposition of 3-methyl-1,2,4-oxadiazole were obtained by Nuclear Magnetic Resonance Spectra (NMR) employing the following technique:

3-Methyl-1,2,4-oxadiazole (density 1.10 gm/ml) at room temperature is mixed with distilled water in various proportions to obtain aqueous mixtures containing 0.1, 0.3, 1, 3 and 10 moles of water per mole of oxadiazole. All mixtures are single liquid phases. Aqueous mixture or neat liquid, about 0.4 ml., are pipetted into standard glass NMR tubes which then are flame sealed. The tubes are immersed in a constant-temperature oil bath at 80° ±

0.2° C. or 100° ±0.2° C. and are withdrawn periodically for measurement of NMR spectra. The NMR spectra is recorded and then the tube is replaced in the oil bath for further observation. The NMR spectra include resolved single bands for each of the following: oxadiazole methyl (3 protons), oxadiazole ring (1 proton), acetonitrile methyl (3 protons) and water (2 protons). Cyanic and cyanuric acids are not recorded. Extent of decomposition is determined by comparison of the oxadiazole methyl and the acetonitrile methyl areas. Cyanuric acid does not interfere even though it is insoluble in some mixtures.

The results of the experiments described above are set forth in the following tables.

TABLE 1

3-Methyl-1,2,4-Oxadiazole (Decomposition 80° C.)

| MOLE $H_2O$ | % Decomposition Hours | | | | | | |
|---|---|---|---|---|---|---|---|
| | 1 | 2 | 4 | 8 | 15 | 35 | 102 |
| 0 | 0 | 0 | 5 | 50 | 95 | 100 | — |
| 0.1 | 0 | 0.5 | 16 | 42 | 90 | 100 | — |
| 0.3 | 0.5 | 2.5 | 9 | 10 | 11 | 18 | 38 |
| 1.0 | 0 | 0.5 | 0.5 | 1 | 1.5 | 5 | 15 |
| 3.0 | 0.5 | 1 | 2 | 3 | 5 | 14 | 50 |
| 10.0 | 1 | 2 | 6 | 11 | 20 | 53 | 100 |

TABLE 2

3-Methyl-1,2,4-Oxadiazole (Decomposition 100° C.)

| MOLES $H_2O$ | % Decomposition Hours | | | | |
|---|---|---|---|---|---|
| | 2 | 4 | 8 | 16 | 32 |
| 0 | 77 | 100 | — | — | — |
| 0.1 | 77 | 95 | 100 | — | — |
| 0.3 | 24 | 37 | 59 | 83 | 97 |
| 1.0 | 4 | 8 | 12 | 22 | 44 |
| 3.0 | 5 | 9 | 20 | 47 | 95 |
| 10.0 | 15 | 34 | 64 | 97 | 100 |

The rate data for the decomposition of 3-methyl-1,2,4-oxadiazole both neat and in aqueous mixture (rate for the appearance of acetonitrile) may be seen in TABLES 1 and 2. The data confirm that the stabilizing effect of water on the oxadiazole is directly dependent upon the molar ratio of water to oxadiazole and clearly demonstrates that maximum stability is achieved at both 80° and 100° C. when this molar ratio is 1:1; the stability of the mixtures falling off the maximum as the molar ratio is either increased or decreased. Further, the data indicate that with equimolar mixtures a relatively constant reaction rate is observed which is about 10 times greater at 100° C. than at 80° C. (i.e. the decomposition rate can be expected to vary by a factor of 10 per 20° C. change in temperature).

In order to more clearly define the critical range of the molar ratio of water to oxadiazole, a similar experiment was conducted at 80° C. employing more narrow increments of the molar ratio of water to oxadiazole. In this experiment, the same technique as described above was employed except that the decomposition rate of neat 3-methyl-1,2,4-oxadiazole was compared with aqueous mixtures of the axadiazole containing 0.5, 0.75, 1, 1.25, 1.5, 1.75, 2, 2.25, 2.5, 2.75 and 3 moles of water per mole of oxadiazole. The results of this experiment are set forth in the following table:

TABLE 3

3-Methyl-1,2,4-Oxadiazole (Decomposition 80° C.)

| MOLES $H_2O$ | % Decomposition Hours | | |
|---|---|---|---|
| | 15.5 | 37 | 59 |
| 0 | 57.5 | 99 | 100 |
| 0.5 | 7.5 | 9.5 | 10 |
| 0.75 | 2.5 | 4 | 4.5 |
| 1.0 | 0 | 1 | 4 |
| 1.25 | 0 | 4 | 5 |
| 1.5 | 0 | 5 | 7.5 |
| 1.75 | 0 | 5 | 8 |
| 2.0 | 0 | 6.5 | 10.5 |
| 2.25 | 0 | 8 | 13 |
| 2.5 | 0 | 9 | 15 |
| 2.75 | 0 | 9.5 | 17 |
| 3.0 | 0 | 13 | 20 |

The data summarized in TABLE 3 clearly confirms applicants' previous discovery that the stabilizing effect of water on the oxadiazole depends directly upon the molar ratio of water to oxadiazole and confirms also that maximum stabilization is achieved in equimolar mixtures of water and the oxadiazole. In view of the relatively constant reaction rate observed and the variation of that rate with change in temperature (i.e. decomposition rate varies by a factor of 10 per 20° C. change in temperature), the data in TABLE 3 may be reliably extrapolated to room temperature (20° C.) and shows that, in equimolar mixture of water and oxadiazole at room temperature, about 1% decomposition of oxadiazole would be expected per 1000 days (3 years). Similar extrapolation of the data of TABLE 3 shows that, over the same period, about 9% decomposition of the oxadiazole would be expected in mixtures wherein the water to oxadiazole ratio is 0.5:1 and that about 6% decomposition of the oxadiazole would be expected in mixture wherein the water to oxadiazole ratio is 2:1, thus, within the range 0.5:1 to 2:1 (water to oxadiazole) a maximum decomposition of oxadiazole of about 3% per year would be anticipated. Such decomposition rate is well within the limits required for commercially feasible utilization of the oxadiazole in anthelmintic therapy.

The aqueous oxadiazole compositions described above may be employed in a variety of dosage forms, both oral and injectable, in the treatment and control of helminthiasis either with or without further formulation. Thus, conventiently, they may be administered by parenteral injection, by inhalation, by admixture with drinking water or by drench in the usual manner. Where desired, for ease of administration, the aqueous oxadiazole formulations of this invention, immediately prior to use, may be further diluted with water or with other pharmaceutically acceptable liquid carriers. Also, these aqueous oxadiazole formulations may be employed in solid dosage forms for oral administration by filling into sealed hard gelatin capsules or by adsorbing them onto a carrier, such as bentonite, and formulating the wetted adsorbate into coated and sealed tablets, boluses and the like.

In the treatment of helminthiasis, the aqueous oxadiazole compositions of this invention may be administered in a single dose or in multiple doses. Usually, effective anthelmintic response is achieved by administration of a single dose containing from about 5 to about 500 mg./kg. of body weight of the active oxadiazole. The preferred single dosage usually is from about 10 to about 200 mg./kg. of body weight. For ease of administration, these dosages may be subdivided to establish any desired multiple dosage schedule. It will be understood by those skilled in the art, that the dosage required to achieve optimum results in any particular anthelmintic application will vary depending upon factors such as the nature of the host, the oxadiazole employed and the nature and severity of the infection being treated. It is obvious, therefore, that dosages greater or smaller than those disclosed above may be required in particular applications.

In addition, applicants have found that stabilization of 3-loweralkyl-1,2,4-oxadiazoles also can be achieved by employing as the stabilizing agent, instead of water, certain alcohols. Useful alcohols, applicants have discovered, include the lower aliphatic alcohols having from 1 to 4 carbon atoms, such as methanol, ethanol, propanol, isopropanol, butanol and isobutanol, ethylene glycol and propylene glycol and glycerol; polyethylene glycols having a molecular weight of about 200 to 800; mono-, di- and tripropanol amine; phenyl substituted lower alcohols such as benzyl alcohol and alkyl and benzyl esters thereof; and loweralkyl esters of hydroxy loweralkanoic acids having from 1 to 4 carbon atoms in the ester and alkanoic acid moieties, such as ethyl glycolate, ethyl lactate, and propylglycolate; aniline and mono or di-loweralkyl derivatives thereof; other such as ethyl ether and tetrahydrofuran; benzene and derivatives thereof such as nitro, loweralkoxy and amino derivatives. Applicants have found that a stabilizing effect on 3-loweralkyl-1,2,4-oxadiazoles similar to that observed with water is obtained when these alcohols are employed as the stabilizing agent. The degree of stabilization achieved, as with water, is dependent upon the molar ratio of alcohol to oxadiazole in the mixture. The precise molar ratio required for maximum stabilizing effect will vary depending upon the alcohol employed as the stabilizing agent. Applicants have found, however, that mixtures wherein the 3-loweralkyl-1,2,4-oxadiazole is sufficiently stable to make feasible its commercial utilization in anthelmintic therapy are obtained when the molar ratio of alcohol to oxadiazole falls within the range of about 0.1:1 to about 2:1. It is contemplated that such alcoholic 3-loweralkyl-1,2,4-oxadiazole formulations will be employed, in the manner already described, in the treatment and control of helminthiasis.

In the manner previously described solutions of 3-methyl-1,2,4-oxadiazole is ethylene glycol were tested for stability at 80° C. The following data was obtained:

| Amount | % Decomposition at indicated time in hours | | | |
|---|---|---|---|---|
| | 14 ¾ | 37 ¼ | ¾ | 86 ¼ |
| 0.05 mole | 60.2 | 100 | 100 | 100 |
| 0.1 mole | 4.1 | 16.0 | 19.8 | 32.9 |
| 0.15 mole | 1.7 | 2.5 | 2.6 | 3.5 |
| 0.2 mole | 1.9 | 3.0 | 3.0 | 3.8 |
| 0.25 mole | 1.8 | 3.1 | 3.5 | 44.8 |

Similarly propylene glycol was tested at 80° C.

| Amount | % Decomposition at indicated time in hours | | |
|---|---|---|---|
| | 14.5 | 37 | 172 ¼ |
| 1 mole | 3.7 | 8.0 | 50.4 |
| 0.75 mole | 3.1 | 7.0 | 46.3 |
| 0.5 mole | 2.8 | 6.1 | 48.8 |
| 0.25 mole | 18.7 | 29.3 | 83.0 |
| control | 59.7 | 80.0 | 100.0 |

| Amount | % Decomposition at indicated time in hours | | | |
|---|---|---|---|---|
| | 14.5 | .36 | 64.5 | 157.5 |
| 0.1 mole | 2.7 | 36.0 | 61.0 | 94.5 |
| 0.2 mole | 2.3 | 2.7 | 3.9 | 44.8 |
| 0.3 mole | 2.5 | 3.2 | 5.3 | 38.6 |
| 0.4 mole | 2.7 | 3.8 | 7.8 | 41.6 |
| 0.5 mole | 3.9 | 4.0 | 9.7 | 43.5 |
| 0.6 mole | 3.2 | 4.9 | 9.9 | 46.3 |
| 0.7 mole | 3.3 | 5.2 | 11.6 | 49.5 |
| 0.8 mole | 3.0 | 5.9 | 11.4 | 44.7 |
| 0.9 mole | 3.0 | 7.0 | 13.4 | 48.5 |
| 1.0 mole | 3.4 | 7.0 | 13.1 | 46.1 |
| control | 74.5 | 82.0 | 89.0 | 100.0 |

In addition to the foregoing tests, experiments were conducted with various other solvents in order to determine the amount of decomposition which resulted from such solutions. The tests were conducted at 80° C. and the results calculated using the NMR techniques previously described.

| Additive | Amount | % Decomposition at indicated time in hours | | | |
|---|---|---|---|---|---|
| | | 2 | 16 | 40 | 136 |
| Control | | 0 | 60 | 100 | |
| Methanol | 1 mole | 0 | 1.6 | 3.07 | 13.7 |
| Ethanol | 1 mole | 0 | 4.8 | 48.3 | 54.5 |
| Glycol | 1 mole | 0 | 3.3 | 11.7 | 53.1 |
| Ethanolamine | 1 mole | 0 | 34 | 40 | |
| Diethanolamine | 1 mole | 17 | 17.8 | 22.8 | 52.6 |
| Aniline | 1 mole | 0 | 0 | 0 | 0 |

| Additive | Amount | 14.5 | 36 | 57 | 119 |
|---|---|---|---|---|---|
| Benzene | 1 mole | 0 | 39.0 | 62.5 | |
| n-Propanol | 1 mole | 18.5 | 31.4 | 36.0 | |
| Solketal | 1 mole | 40.0 | 57.7 | 66.0 | |
| Glycol | 0.5 mole | 1.67 | 39.9 | 9.4 | 19.2 |
| Polyethylene glycol (400) | 1 mole | 13.65 | 27.4 | 40.8 | |

| Additive | Amount | 15 | 22 | 77 | 102.75 |
|---|---|---|---|---|---|
| Control | | 68.5 | 100 | | |
| Nitrobenzene | 1 mole | 37.0 | 60.4 | 79.0 | 90.0 |
| 0-Anisidine | 1 mole | 0 | 0 | 0 | 0 |
| N,N Dimethylaniline | 1 mole | 0 | 0 | 22.2 | 37.3 |
| Methylbenzoate | 1 mole | 0 | 31.6 | 93.5 | 100 |
| Anisole | 1 mole | 0 | 8.0 | 71.5 | 80.5 |
| Benzylalcohol | 1 mole | 0 | 0 | 22.2 | 26.5 |
| Ethylether | 1 mole | 0 | 0 | 71.8 | 77.5 |
| Ethyllactate | 1 mole | 18.7 | 28.1 | 62.2 | 70.0 |
| Diethylphthalate | 1 mole | 0 | 18.4 | 93 | 100.00 |
| Furan | 1 mole | 0 | 21.8 | 83.0 | 84.5 |
| Propyleneglycol | 1 mole | 27.2 | 31.7 | 50.0 | 57.0 |

| Additive | Amount | 16.5 | 38 | 59 |
|---|---|---|---|---|
| Acetone | 1 mole | 0 | 18 | 39.5 |
| Tetrahydrofuran | 1 mole | 9.9 | 47.7 | 60.0 |

-continued

| | | | | |
|---|---|---|---|---|
| Thiophene | 1 mole | 7.0 | 56.5 | 78.6 |
| 4-Trifluoromethyl-aniline | 1 mole | 0 | 0 | 0 |

| Additive | Amount | 14.5 | 36.5 |
|---|---|---|---|
| Benzylbenzoate | 1 mole | 5.5 | 81.9 |
| Glycol | 0.25 mole | 2.25 | 2.9 |
| Glycol | 0.5 mole | 3.2 | 6.0 |
| Glycol | 0.75 mole | 3.2 | 7.9 |
| Glycol | 1 mole | 4.7 | 8.5 |
| Isopropanol | 1 mole | 42.5 | 52.2 |

The above data indicates that a broad spectrum of organic compounds are effective at stabilizing 3-methyl-1,2,4-oxadiazole. While it is obvious that some compounds are superior to others in their ability to stabilize the anthelmintic compound to one skilled in the art. It is also obvious that all of the stabilizing agents offer superior stability to the unstabilized compounds.

The preferred stabilizing agents are the alcohols, (loweralkanols, the glycols, benzyl alcohol) and aniline and derivatives thereof, particularly N,N, loweralkyl derivatives thereof.

3-Methyl-1,2,4-oxadiazole, stabilized with the above organic stabilizing agents may be employed in anthelmintic compositions for administration to animals infected with helminths in a manner similar to the compositions employing water stabilized 3-methyl-1,2,4-oxadiazole described above.

The subject matter which applicants regard as their invention is particularly pointed out and distinctly claimed as follows.

What is claimed is:

1. A stabilized 3-loweralkyl-1,2,4-oxadiazole anthelmintic composition comprising an anthelmintically effective quantity of a 3-loweralkyl-1,2,4-oxadiazole in homogeneous mixture with a stabilizing agent selected from the group consisting of methanol, ethanol, ethylene glycol, propylene glycol, glycerol, aniline, N-methlaniline or N,N-dimethylaniline, said mixture containing from 0.1 to 2.0 moles of stabilizing agent per mole of oxadiazole.

2. The composition of claim 1 wherein the stabilizing agent is a loweraliphatic alcohol, aniline or mono- or di-loweralkyl substituted aniline.

3. The composition of claim 1 wherein the stabilizing agent is methanol or ethanol.

4. The composition of claim 1 wherein the stabilizing agent is ethylene glycol, propylene glycol or glycerol.

5. The composition of claim 1 wherein the stabilizing agent is aniline.

6. The composition of claim 1 wherein the stabilizing agent is N-methyl aniline or N,N-dimethyl aniline.

7. A method for the treatment and control of helminthiasis which comprises administering to a host infected with helminths an anthelmintically effective quantity of an anthelmintic formulation containing a 3-loweralkyl-1,2,4-oxadiazole in homogeneous mixture with a stabilizing agent selected from the group consisiting of methanol, ethanol, ethylene glycol, propylene glycol, glycerol, aniline, N-methylaniline or N,N-dimethylaniline, said mixture containing from 0.1 to 2.0 moles of stabilizing agent per mole of oxadiazole.

8. The method of claim 7 wherein the anthelmintically effective dose contains from 5 to 500 mg./kg. of body weight of active oxadiazole.

9. The method of claim 7 wherein the anthelmintically effective dose contains from 10 to 200 mg./kg. of body weight of active oxadiazole.

10. The method of claim 7 wherein the oxadiazole is 3-methyl-1,2,4-oxadiazole.

11. The method of claim 10 wherein the mixture contains 0.75 to 1.25 moles of stabilizing agent per mole of oxadiazole.

12. The method of claim 10 wherein the mixture contains 1 mole of stabilizing agent per mole of oxadiazole.

13. The method of claim 7 wherein the stabilizing agent is methanol or ethanol.

14. The method of claim 7 wherein the stabilizing agent is ethylene glycol, propylene glycol or glycerol.

15. The method of claim 7 wherein the stabilizing agent is aniline.

16. The method of claim 7 wherein the stabilizing agent is N-methyl aniline or N,N-dimethyl aniline.

* * * * *